United States Patent [19]

Oda et al.

[11] Patent Number: 5,407,902
[45] Date of Patent: Apr. 18, 1995

[54] METHOXYIMINOACETIC ACID DERIVATIVE AND AGRICULTURAL/HORTICULTURAL FUNGICIDE CONTAINING THE SAME AS ACTIVE INGREDIENT

[75] Inventors: Masatsugu Oda, Yokohama; Manabu Katsurada, Sagamihara; Hirofumi Tomita, Machida, all of Japan

[73] Assignee: Mitsubishi Kasei Corporation, Tokyo, Japan

[21] Appl. No.: 130,560

[22] Filed: Oct. 1, 1993

[30] Foreign Application Priority Data

Oct. 2, 1992 [JP] Japan ................... 4-265193
Nov. 5, 1992 [JP] Japan ................... 4-296140
Jul. 15, 1993 [JP] Japan ................... 5-175497

[51] Int. Cl.$^6$ ........................... A01N 25/32
[52] U.S. Cl. ................... 504/336; 504/269;
504/289; 504/293; 504/295; 504/309; 504/260;
564/167; 564/162; 548/204; 549/77; 549/336;
549/441; 558/49; 546/337
[58] Field of Search ............... 564/167, 162; 548/204;
549/441, 366, 77; 558/49; 546/337; 504/269,
289, 293, 295, 309, 336, 260

[56] References Cited

U.S. PATENT DOCUMENTS

| | | | |
|---|---|---|---|
| 5,194,662 | 3/1993 | Brand et al. | 560/35 |
| 5,254,717 | 10/1993 | Grammenos et al. | 560/35 |

FOREIGN PATENT DOCUMENTS

| | | |
|---|---|---|
| 0463488 | 1/1992 | European Pat. Off. |
| 0499823 | 8/1992 | European Pat. Off. |
| 515901 | 12/1992 | European Pat. Off. |
| 0515901 | 12/1992 | European Pat. Off. |
| 92/13830 | 8/1992 | WIPO |

*Primary Examiner*—José G. Dees
*Assistant Examiner*—Samuel Barts
*Attorney, Agent, or Firm*—Foley & Lardner

[57] ABSTRACT

A methoxyiminoacetic acid derivative represented by the following formula (I):

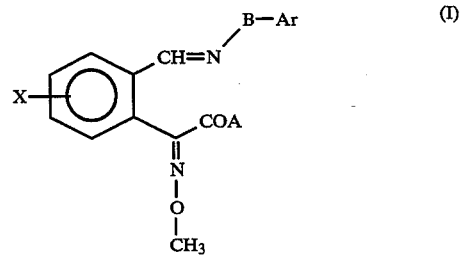

wherein X represents a hydrogen atom, a halogen atom, an alkyl group having 1 to 4 carbon atoms or an alkoxy group having 1 to 4 carbon atoms; A represents a methoxy group or a methylamino group; when A is a methoxy group, B represents —O—CO— or —N=C(R$^1$)— and when A is a methylamino group, B represents —O—CR$^1$R$^2$—, wherein R$^1$ and R$^2$ independently represent a hydrogen atom, an alkyl group having 1 to 4 carbon atoms or a trifluoromethyl group; and Ar represents an optionally substituted aryl group or an optionally substituted heteroaryl group, and an agricultural/horticultural fungicide containing the same as an active ingredient.

17 Claims, No Drawings

METHOXYIMINOACETIC ACID DERIVATIVE AND AGRICULTURAL/HORTICULTURAL FUNGICIDE CONTAINING THE SAME AS ACTIVE INGREDIENT

FIELD OF THE INVENTION

This invention relates to a novel methoxyiminoacetic acid derivative and an agricultural/horticultural fungicide containing the same as an active ingredient.

BACKGROUND OF THE INVENTION

It has been known that certain methoxyiminoacetic acid derivatives have biological activities including fungicidal activities. For example, a compound of the formula:

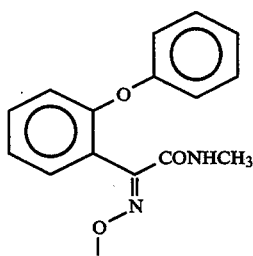

is described in EP 398692. Further a compound of the formula:

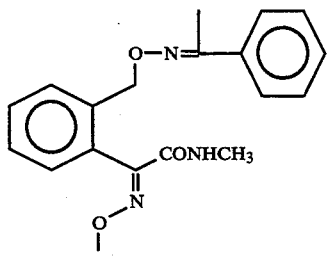

is described in WO92/13830 and EP 463488. Furthermore, a compound of the formula:

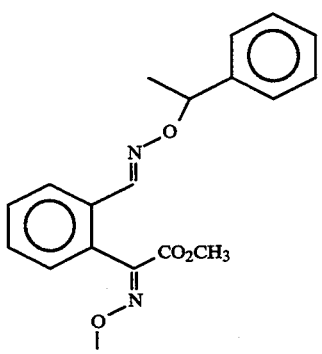

is described in EP 499823. Also, a compound of the formula:

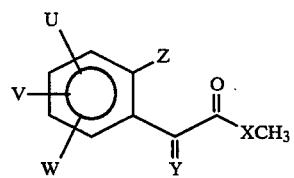

is described in EP515901.

However, these compounds are not always satisfactory as an agricultural/horticultural fungicide, as will be shown in Test Examples hereinafter.

SUMMARY OF THE INVENTION

Under these circumstances, the present inventors have paid their attention to these methoxyiminoacetic acid derivatives and conducted extensive studies thereon. As a result, it has successfully been found out that a methoxyiminoacetic acid derivative having a specific structure has a potent fungicidal activity as well as an excellent systemic and residual activity for plants, thus completing the present invention.

Accordingly, the gist of the present invention resides in a methoxyiminoacetic acid derivative represented by the following formula (I):

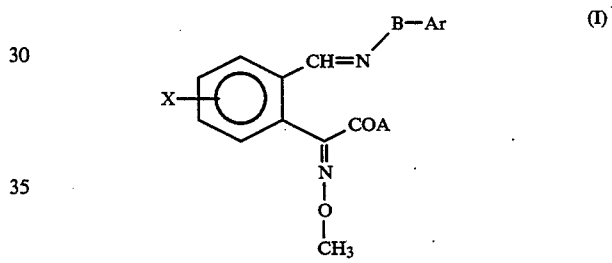

wherein X represents a hydrogen atom, a halogen atom, an alkyl group having 1 to 4 carbon atoms or an alkoxy group having 1 to 4 carbon atoms; A represents a methoxy group or a methylamino group; when A is a methoxy group, B represents —O—CO— or —N=C(R$^1$)— and when A is a methylamino group, B represents —O—CR$^1$R$^2$—, wherein R$^1$ and R$^2$ independently represent a hydrogen atom, an alkyl group having 1 to 4 carbon atoms, a cyano group or a trifluoromethyl group; and Ar represents an optionally substituted aryl group or an optionally substituted heteroaryl group, and an agricultural/horticultural fungicide containing the same as an active ingredient.

DETAILED DESCRIPTION OF THE INVENTION

Now, the present invention will be described in detail.

The methoxyiminoacetic acid derivative of the present invention is the one represented by the above formula (I). In the above formula (I), X represents a hydrogen atom; a halogen atom (for example, fluorine, chlorine, bromine); an alkyl group having 1 to 4 carbon atoms (for example, methyl, ethyl, n-propyl, iso-propyl, n-butyl, sec-butyl); or an alkoxy group having 1 to 4 carbon atoms (for example, methoxy, ethoxy, iso-propoxy, n-butoxy). It preferably represents a hydrogen atom or a halogen atom, still preferably a hydrogen atom.

A represents a methoxy group or a methylamino group. It preferably represents a methylamino group.

When A is a methoxy group, B represents —O—CO— or —N=C(R¹)—. When A is a methylamino group, B represents —O—CR¹R²—. R¹ and R² independently represent a hydrogen atom; an alkyl group having 1 to 4 carbon atoms (for example, methyl, ethyl, n-propyl, iso-propyl, n-butyl, sec-butyl); a cyano group; or a trifluoromethyl group. It preferably represents a hydrogen atom, a cyano group or a methyl group.

Ar represents an aryl group (for example phenyl, naphthyl) which may be optionally substituted by the following groups; or a heteroaryl group (for example, pyridyl, thienyl, thiazolyl) which may be optionally substituted by the following groups. It preferably represents a phenyl group which may be optionally substituted by the following groups, a naphthyl group, a thienyl group which may be optionally substituted by the following groups, or a thiazolyl group which may be optionally substituted by the following groups.

Examples of the substituents for the above-mentioned aryl group include a cyano group; a halogen atom (for example, fluorine, chlorine, bromine); an alkyl group having 1 to 6 carbon atoms (for example, methyl, ethyl, n-propyl, iso-propyl, n-butyl, sec-butyl); an alkenyl group having 2 to 4 carbon atoms (for example, ethenyl, propenyl) optionally substituted by a halogen atom; a haloalkyl group having 1 to 4 carbon atoms (for example, trifluoromethyl, difluoromethyl, trichloromethyl, dichlorodifluoroethyl); an alkoxy group having 1 to 6 carbon atoms (for example, methoxy, ethoxy, iso-propoxy, n-butoxy) optionally substituted by a halogen atom or a cycloalkyl group having 3 to 6 carbon atoms; an alkylcarbonyloxy group having 1 to 7 carbon atoms (for example, acetoxy, propionyloxy, pivaloyloxy) optionally substituted by a halogen atom; an acylamino group having 1 to 7 carbon atoms (for example, acetoamino, propionylamino) optionally substituted by a halogen atom; an alkylthio group having 1 to 6 carbon atoms (for example, methylthio, ethylthio, iso-propylthio, n-butylthio) optionally substituted by a halogen atom; an aryl group (for example, phenyl) optionally substituted by an alkyl group having 1 to 4 carbon atoms or a halogen atom; an aryloxy group (for example, phenoxy) optionally substituted by an alkyl group having 1 to 4 carbon atoms or a halogen atom; an alkylsulfonyloxy group having 1 to 6 carbon atoms (for example, methanesulfonyloxy or ethanesulfonyloxy) optionally substituted by a halogen atom; an alkenyloxy group having 2 to 6 carbon atoms (for example, propenyloxy) optionally substituted by a halogen atom; and an alkynyloxy group having 2 to 6 carbon atoms (for example, propargyloxy). From among these substituents, those adjacent to each other may be combined together to give, for example, a methylenedioxy or ethylenedioxy group and form a fused ring together with an aryl group. The number of substituents is from 1 to 5, preferably from 1 to 2. When Ar has two or more substituents, they may be the same or different each other. Preferable examples of substituents for an aryl group include an alkyl group having 1 to 4 carbon atoms, a halogen atom, an alkoxy group having 1 to 4 carbon atoms which may be optionally substituted by a halogen atom (preferably fluorine), an acylamino group having 1 to 4 carbon atoms which may be optionally substituted by a halogen atom (preferably fluorine), an alkylthio group having 1 to 3 carbon atoms, an alkylsulfonyloxy group having 1 to 3 carbon atoms which may be optionally substituted by a halogen atom (preferably fluorine) and a trifluoromethyl group.

Examples of the substituents for the above-mentioned heteroaryl group include a cyano group; a halogen atom (for example, fluorine, chlorine, bromine); an alkyl group having 1 to 6 carbon atoms (for example, methyl, ethyl, n-propyl, iso-propyl, n-butyl, sec-butyl); a haloalkyl group having 1 to 4 carbon atoms (for example, trifluoromethyl, difluoromethyl, trichloromethyl, dichlorodifluoroethyl); and an alkoxy group having 1 to 6 carbon atoms (for example, methoxy, ethoxy, iso-propoxy, n-butoxy) optionally substituted by a halogen atom or a cycloalkyl group having 3 to 6 carbon atoms. The number of substituents, which may be the same or different each other, is from 1 to 2. Among these substituents, an alkyl group having 1 to 4 carbon atoms, a halogen atom and a trifluoromethyl group may be cited as preferable ones.

The compounds of the present invention are each a novel one and can be prepared, for example, in accordance with the following reaction scheme:

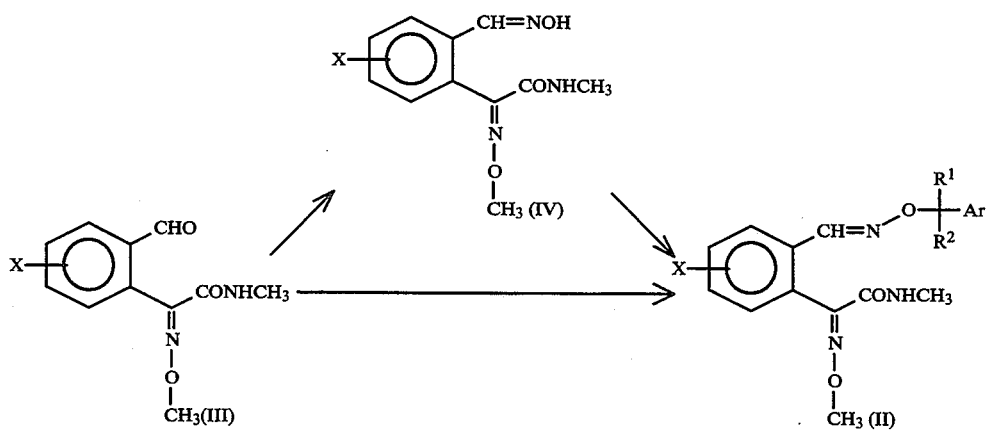

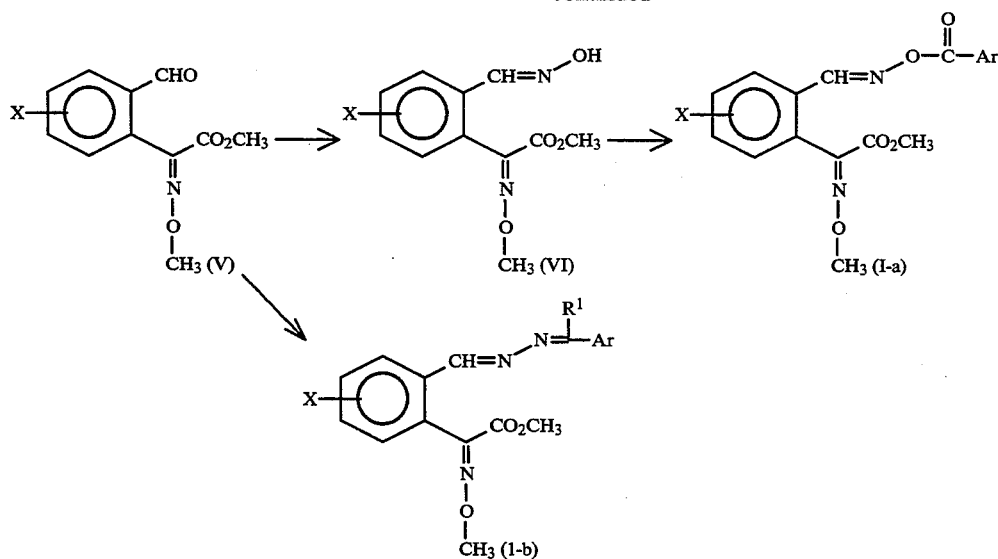

[wherein X, $R^1$, $R^2$ and Ar are as defined in the above formula (I)].

The compounds represented by the above formulae (II) and I-a) can be prepared by, respectively, reacting the benzaldehyde derivatives of the above formulae (III) and (V) with a hydroxylamine hydrochloride and reacting the oxime derivatives (IV) and (VI) thus obtained with the corresponding benzyl halide derivative or benzoyl halide derivative in the presence of an appropriate base in an inert solvent (for example, diethyl ether, tetrahydrofuran, dimethylformamide, dimethylsulfoxide, methylene chloride, dichloroethane).

Examples of the base to be used in the above reaction include an alkali metal hydride (for example, sodium hydride); an alkali metal alcoholate (for example, sodium methylate); an alkali metal carbonate (for example, potassium carbonate); an alkali metal hydroxide (for example, potassium hydroxide); a tertiary amine (for example, N-methylmorpholine, triethylamine); and an aromatic base (for example, pyridine, picoline).

In some cases, the compound of the above formula (II) can be directly obtained by reacting the benzaldehyde derivative (III) with o-substituted hydroxylamine in an inert solvent such as an alcohol.

The compound of the above formula (I-b) can be obtained by reacting the benzaldehyde derivative represented by the above formula (V) with the corresponding hydrazone derivative in an inert solvent such as an alcohol.

The above-mentioned compounds of formulae (III) and (V) as starting materials can be produced in accordance with the method described in EP398693, EP499823 or the like.

In some cases, the compound of the above formula (II) can be prepared in accordance with the following reaction scheme:

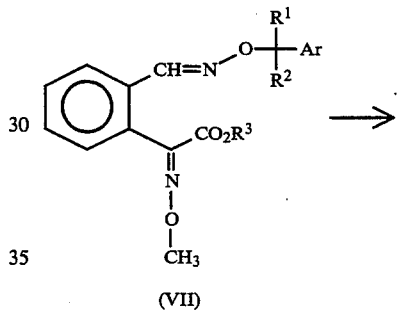

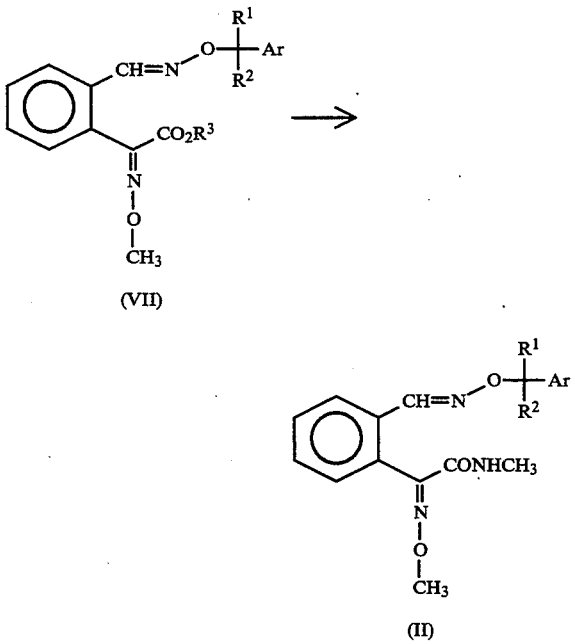

[wherein $R^1$, $R^2$ and Ar are as defined in the above formula (I) and $R^3$ represents an alkyl group having 1 to 10 carbon atoms].

The compounds of the above formula (II) can be obtained by reacting an ester derivative (VII) with methylamine in an inert solvent such as an alcohol.

The compounds of the above formulae (II), (I-a) and (I-b) each exists as isomers at the methoxyimino moiety. Each isomer can be separated each other from the mixture of isomers which is obtained usually, by a conventional manner such as column chromatography. Each of E-, X-mixture or Z-isomer can be converted to the E-isomer which shows high activities, by treating with an acid (for example, hydrochloric acid, sulfuric acid, methanesulfonic acid) in an alcohol solvent (for example, methanol, ethanol).

The compounds of the present invention thus obtained are each a novel one having an excellent fungicidal activity. They exert excellent preventive effects on various phytopathogenic fungi, which makes them useful as an agricultural/horticultural fungicide.

For example, these compounds exert high activity on rice blast (*Pyricularia oryzae*), rice sheath blight (*Rhizoctonia solani*), wheat powdery mildew (*Erysiphe graminis f. sp. hodei*), various leaf rusts of wheat and barley (e.g. *Puccinia recondita*), gray mold of vegetables and fruit trees (*Botrytis cinerea*) and late blight of various crops (*(Phytophthora infestance*). Further, they have prolonged residual activity and excellent systemic action in plants, which makes them highly useful as an agricultural/horticultural fungicide.

When the compound of the present invention is to be used as an agricultural/horticultural fungicide, it may be applied as such. However, it is preferable to formulate said compound into, for example, emulsifiable concentrate, wettable powder, dust or granules by blending with adjuvants in a conventional manner to thereby ensure the effective dispersion of the active ingredient at the application.

When the agricultural/horticultural fungicide according to the present invention is to be formulated into an emulsifiable concentrate, 10 to 80 parts by weight (hereinafter referred to as "parts") (preferably 10 to 70 parts) of the compound of the present invention, 10 to 90 parts (preferably 20 to 80 parts) of a solvent and 3 to 20 parts (preferably 5 to 15 parts) of a surfactant are mixed together at an appropriate ratio. At the usage, the obtained mixture is diluted with water to a definite concentration and applied by, for example, spraying.

When the agricultural/horticultural fungicide of the present invention is to be used as a wettable powder, 5 to 80 parts (preferably 10 to 70 parts) of the compound of the present invention, 10 to 90 parts (preferably 20 to 80 parts) of a filler and 1 to 20 parts (preferably 3 to 15 parts) of a surfactant are mixed together at an appropriate ratio. At the usage, the obtained mixture is diluted with, for example, water to a definite concentration and applied, similar to the case of the emulsifiable concentrate.

When the agricultural/horticultural fungicide of the present invention is to be used as a dust, 0.1 to 10 parts (preferably 1 to 5 parts) of the compound of the present invention is uniformly mixed with 90 to 99.9 parts (preferably 95 to 99 parts) of a filler (for example, kaolin, bentonite, talc).

The agricultural/horticultural fungicide of the present invention may further contain other active ingredients such as bactericides, insecticides and miticides, so long as the effects of the active ingredient of the present invention are not deteriorated thereby.

The agricultural/horticultural fungicide of the present invention can be suitably used either in foliar application or in submerged application. In the case of foliar application, the agricultural/horticultural fungicide is usually formulated into an emulsifiable concentrate or a wettable powder and diluted with water so as to give a concentration of the active ingredient of from 10 to 1,000 ppm. then it is applied at a ratio of 100 to 5000 1 per 1 ha.

To further illustrate the present invention in greater detail, the following Examples will be given. However, it is to be understood that the present invention is not restricted thereto but various changes may be restored within the scope thereof.

SYNTHESIS EXAMPLE 1

Synthesis of N-methyl-2-[2-{3-(trifluoromethyl)benzyloxyiminomethyl}phenyl]-2-methoxyiminoacetamide (compound No. 1 in Table 1):

To a solution of 0.53 g of methyl 2-[2-{3-(trifluoromethyl)benzyloxyiminomethyl}phenyl]-2-methoxyiminoacetate in 5 ml of methanol, was added 5 ml of a 40% methylamine/methanol solution and the mixture was stirred at room temperature overnight. After the completion of the reaction, the solvent was distilled off and the residue was recrystallized from ethyl acetate/hexane (1:9). Thus 0.56 g of the title compound was obtained (quantitative yield).

The compound No. 2 in Table 1 and the compound No. 78 in Table 2 were synthesized by repeating the above-mentioned procedure except altering the starting material.

SYNTHESIS EXAMPLE 2

Synthesis of N-methyl-2-{2-(3-chlorobenzyloxyiminomethyl)-phenyl}-2-methoxyiminoacetamide (compound No. 3 in Table 1):

To a solution of 1 g (4.26 mmol) of N-methyl-2-{2-(hydroxyiminomethyl)phenyl}-2-methoxyiminoacetamide and 0.62 g (4.5 mmol) of potassium carbonate in 10 ml of DMF, was added 0.69 g (4.29 mmol) of 3-chlorobenzyl chloride and the mixture was stirred under heating at 110° C. for 3 hours. After cooling, the reaction mixture was poured into water, extracted with ethyl acetate, successively washed with water and a saturated sodium chloride solution and dried over anhydrous sodium sulfate. After concentration in vacuo, the residue was chromatographed over $SiO_2$ to give 0.9 g of the title compound (yield: 58.8%).

The compounds No. 4 to No. 8 and No. 11 to No. 14 in Table 1 were synthesized by repeating the above-mentioned procedure except altering the starting material.

SYNTHESIS EXAMPLE 3

Synthesis of N-methyl-2-[2-{α-methyl-4-(trifluoromethyl)-benzyloxyiminomethyl}phenyl]-2-methoxyiminoacetamide (compound No. 24 in Table 1):

To a solution of 0.6 g (2.7 mmol) of N-methyl-2-(2-formylphenyl)-2-methoxyiminoacetamide in 7 ml of methanol, was added 0.42 g (3.0 mmol) of α-methyl-4-(trifluoromethyl)-benzyloxyamine and the mixture was allowed to stand at room temperature overnight. After the reaction mixture was concentrated in vacuo, the residue was chromatographed over $SiO_2$ to yield 0.89 g of the title compound (yield:95%).

The compounds Nos. 16–18, 20, 21, 23 ,25, 27–29, 31, 32, 35, 38–40, 42, 44, 46, 47, 49–68 and 72 in Table 1 and the compounds Nos. 76, 77 and 79–83 in Table 2 were synthesized by repeating the above-mentioned procedure except altering the starting material.

SYNTHESIS EXAMPLE 4

Synthesis of methyl 2-[2-{4-(3-trifluoromethylphenyl)-2,3-diaza-1,3-pentadienyl}phenyl]-2-methoxyiminoacetate (compound No. 88 in Table 3):

A mixture comprising 1.5 g (6.75 mmol) of methyl 2-(2-formylphenyl)-2-methoxyiminoacetate, 1.37 g (6.75 mmol) of m-trifluoromethylacetophenone hydrazone and 7.5 ml of ethanol was heated under reflex for 3 hours. After vacuum concentration, the residue was chromatographed over SiO$_2$ to give 2.48 g of the title compound (yield: 86.6%).

The compounds No. 86, No. 87, No. 89 and No. 90 in Table 3 were synthesized by repeating the above-mentioned procedure except altering the starting material.

SYNTHESIS EXAMPLE 5

Synthesis of methyl 2-[2-{4-(trifluoromethyl)benzyloxyiminomethyl}phenyl]-2-methoxyiminoacetate compound No. 91 in Table 3):

To a mixture comprising 0.60 g (2.53 mmol) of methyl 2-{2-(hydroxyiminomethyl)phenyl}-2-methoxyiminoacetate, 1 ml of triethylamine and 5 ml of dichloromethane, was added 0.80 g (3.8 mmol) of p-trifluoromethylbenzoic acid chloride under ice cooling. After stirring at room temperature for 12 hours, the reaction mixture was poured into water and extracted with ethyl acetate. Then it was successively washed with eater and a saturated sodium chloride solution and dried over anhydrous sodium sulfate. After vacuum concentration, the residue was chromatographed over SiO$_2$ to give 0.31 g of the title compound (yield: 30.0%).

TABLE 1

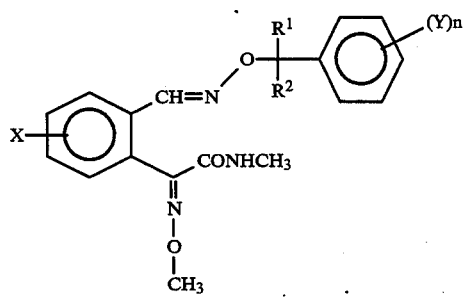

| Compound No. | R$^1$ | R$^2$ | X | (Y)$_n$ | Property |
|---|---|---|---|---|---|
| 1 | H | H | H | 3-CF$_3$ | m.p. 93–97° C. |
| 2 | H | H | H | 4-CF$_3$ | nD 1.5505/25° C. |
| 3 | H | H | H | 3-Cl | m.p. 90–93° C. |
| 4 | H | H | H | 4-Cl | m.p. 119–123° C. |
| 5 | H | H | H | 3-CH$_3$ | m.p. 90–93° C. |
| 6 | H | H | H | 4-CH$_3$ | m.p. 148–150° C. |
| 7 | H | H | H | 2,5-(CH$_3$)$_2$ | m.p. 106.5–107° C. |
| 8 | H | H | H | 3-OCH$_3$ | viscous |
| 9 | H | H | H | 4-OCH$_3$ | viscous |
| 10 | H | H | H | 3-OCF$_3$ | viscous |
| 11 | H | H | H | 4-OCF$_3$ | m.p. 96–97° C. |
| 12 | H | H | H | 2,5-Cl$_2$ | m.p. 148.5–150.5° C. |
| 13 | H | H | H | 3,5-(CF$_3$)$_2$ | m.p. 102.5–105° C. |
| 14 | CH$_3$ | H | H | — | m.p. 107.5–110.2° C. |
| 15 | CH$_3$ | H | H | 2-Cl | viscous |
| 16 | CH$_3$ | H | H | 3-Cl | m.p. 82.5–83° C. |
| 17 | CH$_3$ | H | H | 4-Cl | m.p. 87.5–90.5° C. |
| 18 | CH$_3$ | H | H | 4-Cl | viscous |
| 19 | CH$_3$ | H | H | 3-Br | viscous |
| 20 | CH$_3$ | H | H | 4-Br | amorphous solid |
| 21 | CH$_3$ | H | H | 3,4-Cl$_2$ | m.p. 110.9–111.7° C. |
| 22 | CH$_3$ | H | H | 2,5-Cl$_2$ | viscous |
| 23 | CH$_3$ | H | H | 3-CF$_3$ | m.p. 88.5–89° C. |
| 24 | CH$_3$ | H | H | 4-CF$_3$ | m.p. 70.5–71.5° C. |
| 25 | CH$_3$ | H | H | 4-CF$_3$ | viscous |
| 26 | CH$_3$ | H | H | 2-CH$_3$ | viscous |
| 27 | CH$_3$ | H | H | 3-CH$_3$ | viscous |
| 28 | CH$_3$ | H | H | 4-CH$_3$ | viscous |
| 29 | CH$_3$ | H | H | 2,4-(CH$_3$)$_2$ | viscous |
| 30 | CH$_3$ | H | H | 2,5-(CH$_3$)$_2$ | viscous |
| 31 | CH$_3$ | H | H | 3,4-(CH$_3$)$_2$ | viscous |
| 32 | CH$_3$ | H | H | 4-C$_2$H$_5$ | amorphous solid |

TABLE 1-continued

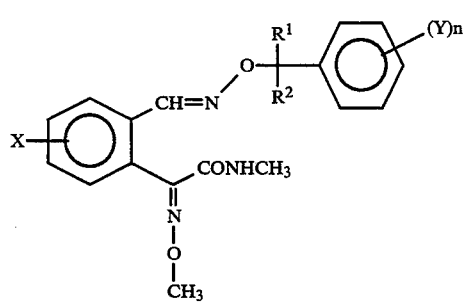

| Compound No. | R$^1$ | R$^2$ | X | (Y)$_n$ | Property |
|---|---|---|---|---|---|
| 33 | CH$_3$ | H | H | 4-C$_3$H$_7$(n) | viscous |
| 34 | CH$_3$ | H | H | 4-C$_3$H$_7$(iso) | viscous |
| 35 | CH$_3$ | H | H | 4-C$_4$H$_9$(tert) | viscous |
| 36 | CH$_3$ | H | H | 2-OCH$_3$ | viscous |
| 37 | CH$_3$ | H | H | 3-OCH$_3$ | viscous |
| 38 | CH$_3$ | H | H | 4-OCH$_3$ | amorphous solid |
| 39 | CH$_3$ | H | H | 4-OC$_2$H$_5$ | amorphous solid |
| 40 | CH$_3$ | H | H | 4-OC$_3$H$_7$(n) | amorphous solid |
| 41 | CH$_3$ | H | H | 3-OC$_3$H$_7$(iso) | amorphous solid |
| 42 | CH$_3$ | H | H | 4-OC$_3$H$_7$(iso) | amorphous solid |
| 43 | CH$_3$ | H | H | 3-propargyloxy | amorphous solid |
| 44 | CH$_3$ | H | H | 4-propargyloxy | amorphous solid |
| 45 | CH$_3$ | H | H | 4-OCH$_2$CH=CCl$_2$ | viscous |
| 46 | CH$_3$ | H | H | 3-OPh | amorphous solid |
| 47 | CH$_3$ | H | H | 4-OPh | amorphous solid |
| 48 | CH$_3$ | H | H | 4-cyclopropyl-methyloxy | viscous |
| 49 | CH$_3$ | H | H | 3-OCF$_3$ | m.p. 82–83° C. |
| 50 | CH$_3$ | H | H | 4-OCF$_3$ | amorphous solid |
| 51 | CH$_3$ | H | H | 3-OCHF$_2$ | viscous |
| 52 | CH$_3$ | H | H | 4-OCHF$_2$ | viscous |
| 53 | CH$_3$ | H | H | 3-OCH$_2$CF$_3$ | viscous |
| 54 | CH$_3$ | H | H | 4-OCH$_2$CF$_3$ | viscous |
| 55 | CH$_3$ | H | H | 4-OCH$_2$CF$_2$CF$_3$ | viscous |
| 56 | CH$_3$ | H | H | 3-OSO$_2$CF$_3$ | viscous |
| 57 | CH$_3$ | H | H | 4-OSO$_2$CF$_3$ | viscous |
| 58 | CH$_3$ | H | H | 3-OSO$_2$C$_2$H$_5$ | viscous |
| 59 | CH$_3$ | H | H | 4-OSO$_2$C$_2$H$_5$ | viscous |
| 60 | CH$_3$ | H | H | 4-NHCOCF$_3$ | viscous |
| 61 | CH$_3$ | H | H | 4-CN | m.p. 122.8–123.7° C. |
| 62 | CH$_3$ | H | H | 4-CN | amorphous solid |
| 63 | CH$_3$ | H | H | 4-Ph | m.p. 65–70.9° C. |
| 64 | CH$_3$ | H | H | 3-SCH$_3$ | viscous |
| 65 | CH$_3$ | H | H | 4-SCH$_3$ | viscous |
| 66 | CH$_3$ | H | H | 3-SC$_3$H$_7$(iso) | viscous |
| 67 | CH$_3$ | H | H | 4-SC$_3$H$_7$(iso) | viscous |
| 68 | CN | H | H | 4-CF$_3$ | viscous |
| 69 | C$_2$H$_5$ | CH$_3$ | H | 4-Cl | viscous |
| 70 | C$_2$H$_5$ | H | H | 4-OCOC$_2$H$_5$ | viscous |
| 71 | C$_2$H$_5$ | H | H | 4-OCF$_3$ | viscous |
| 72 | CN | H | H | — | viscous |
| 73 | CF$_3$ | H | H | 4-CF$_3$ | viscous |
| 74 | CH$_3$ | H | 3-Cl | — | viscous |
| 75 | CH$_3$ | H | 3-Cl | 4-CF$_3$ | viscous |

*The compounds No. 18, No. 25 and No. 62 are respectively isomers of the compounds No. 17, No. 24 and No. 61 at the benzyloxyimino moiety.

**Although E- and Z-isomers at the methoxyimino moiety exist, the properties of E-isomers alone are given in the above table.

TABLE 2

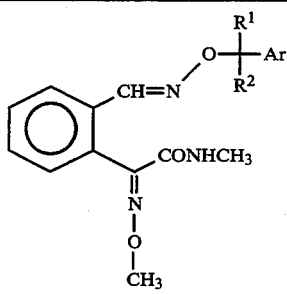

| Compound No. | R¹ | R² | Ar | Property |
|---|---|---|---|---|
| 76 | CH₃ | H | 2-naphthyl | amorphous solid |
| 77 | CH₃ | H | 1-naphthyl | viscous |
| 78 | H | H | 6-chloropyridine-2-yl | viscous |
| 79 | CH₃ | H | 6-trifluoromethyl-pyridine-2-yl | viscous |
| 80 | CH₃ | H | 3,4-methylenedioxyphenyl | amorphous solid |
| 81 | CH₃ | H | 3,4-ethylenedioxyphenyl | viscous |
| 82 | CH₃ | H | 5-chloro-2-thienyl | viscous |
| 83 | CH₃ | H | 2-chloro-4-methylthiazole-5-yl | viscous |
| 84 | CH₃ | CH₃ | 2,4-dimethylthiazole-5-yl | viscous |
| 85 | C₂H₅ | H | 2-t-butylthiazole-5-yl | viscous |

*Although E- and Z-isomers at the methoxyimino moiety exist, the properties of the E-isomers alone are given in the above table.

TABLE 3

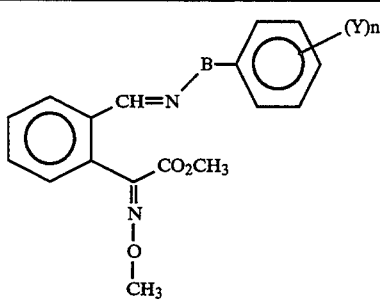

| Compound No. | B | (Y)ₙ | Property |
|---|---|---|---|
| 86 | N=C(CH₃) | 3-CH₃ | 97–104° C. |
| 87 | N=C(CH₃) | 3-Cl | 117–118.5° C. |
| 88 | N=C(CH₃) | 3-CF₃ | 138–138.5° C. |
| 89 | N=C(CH₃) | 4-Cl | 129–132° C. |
| 90 | N=C(CH₃) | 4-CF₃ | 141–144° C. |
| 91 | O—C(O) | 4-CF₃ | nD 1.5474/25 |

*Although E- and Z-isomers at the methoxyimino moiety exist, the properties of the E-isomers alone are given in the above table.

$^1$H-NMR data of the obtained compounds are as follows. [Table 1]

$^1$H-NMR data of compound No. 1 (CDCl₃): 2.89 (3H, d), 3.89 (3H, s), 5.20 (2H, s), 6.73 (1H, brs), 7.18 (1H, dd), 7.39 (1H, dd), 7.42 (1H, d), 7.49 (1H,d) 7.55–7.60 (2H, m), 7.64 (1H, s), 7.76 (1H, dd), 7.97 (1H, s)

$^1$H-NMR data of compound No. 2 (CDCl₃): 2.79 (3H, d), 3.85 (3H, s), 5.18 (2H, s), 6.95 (1H, br), 7.19 (1H, d), 7.32–7.40 (2H, m), 7.47 (2H, d), 7.59 (2H,d), 7.76 (1H, d), 8.03 (1H, s)

$^1$H-NMR data of compound No. 3 (CDCl₃); 2.89 (3H, d), 3.90 (3H, s), 5.11 (2H, s), 6.71 (1H, brs), 7.18 (1H, dd), 7.24–7.30 (3H, m), 7.37 (1H, s), 7.39 (1H,dd), 7.41 (1H, dd), 7.74 (1H, dd), 7.96 (1H, s)

$^1$H-NMR data of compound No. 4 (CDCl₃); 2.89 (3H, d), 3.90 (3H, s), 5.11 (2H, s), 6.69 (1H, brs), 7.17 (1H, dd), 7.32 (4H, s), 7.39 (1H, dd), 7.41 (1H, dd), 7.75 (1H, dd), 7.94 (1H, s)

$^1$H-NMR data of compound No. 5 (CDCl₃); 2.35 (3H, s), 2.83 (3H, d), 3.87 (3H, s), 5.11 (2H, s), 6.71 (1H, brs), 7.11 (1H, d), 7.15–7.27 (4H, m), 7.36 (1H, dd), 7.39 (1H, dd), 7.76 (1H, dd), 7.95 (1H, s)

$^1$H-NMR data of compound No. 6 (CDCl₃); 2.35 (3H, s), 2.88 (3H, d), 3.90 (3H, s), 5.11 (2H, s), 6.67 (1H, brs), 7.17 (2H, d), 7.18 (1H, dd), 7.28 (2H, d), 7.38 (1H, dd), 7.41 (1H, dd), 7.77 (1H, dd), 7.93 (1H, s)

$^1$H-NMR data of compound No. 7 (CDCl₃); 2.33 (3H, s), 2.34 (3H, s), 2.88 (3H, d), 3.91 (3H, s), 5.15 (2H, s), 6.68 (1H, brs), 7.05 (1H, d), 7.08 (1H, d), 7.16 (1H, s), 7.18 (1H, dd), 7.39 (1H, dd), 7.42 (1H, dd), 7.80 (1H, dd), 7.94 (1H, s)

$^1$H-NMR data of compound No. 8 (CDCl₃); 2.86 (3H, s), 3.81 (3H, s), 3.90 (3H, s), 5.15 (2H, s), 6.76 (1H, br), 6.87 (1H, d), 6.96 (1H, s), 6.98 (1H, d), 7.20 (1H, dd), 7.29 (1H, dd), 7.39 (1H, dd), 7.42 (1H, dd), 7.78 (1H, dd), 7.99 (1H, s)

$^1$H-NMR data of compound No. 11 (CDCl₃); 2.88 (3H, d), 3.89 (3H, s), 5.14 (2H, s), 6.71 (1H, br), 7.16–7.24 (3H, m), 7.38–7.44 (4H, m), 7.76 (1H, dd), 7.95 (1H, s), $^1$H-NMR data of compound No. 12 (CDCl₃); 2.90 (3H, d), 3.92 (3H, s), 5.23 (2H, s), 6.75 (1H, brs), 7.19 (1H, dd), 7.22 (1H, dd), 7.30 (1H, d), 7.39–7.45 (3H, m), 7.75 (1H, dd), 8.01 (1H, s)

$^1$H-NMR data of compound No. 13 (CDCl₃); 2.91 (3H, d), 3.89 (3H, s), 5.24 (2H, s), 6.77 (1H, br), 7.18 (1H, dd), 7.37–7.46 (2H, m), 7.76 (1H, dd), 7.83 (3H, s), 7.98 (1H, s)

$^1$H-NMR data of compound No. 14 (CDCl₃); 1.58 (3H, d), 2.86 (3H, d), 3.87 (3H, s), 5.26 (1H, q), 6.56 (1H, br), 7.16 (1H, m), 7.3–7.4 (7H), 7.68 (1H, m), 7.96 (1H, s)

$^1$H-NMR data of compound No. 16 (CDCl₃); 1.55 (3H, d), 2.87 (3H, d), 3.88 (3H, s), 5.22 (1H, q), 6.63 (1H, br), 7.15 (1H, dd), 7.19–7.28 (3H, m), 7.33 (1H, s), 7.36 (1H, dd), 7.39 (1H, dd), 7.67 (1H, dd), 7.96 (1H, s)

$^1$H-NMR data of compound No. 17 (CDCl₃); 1.56 (3H, d), 2.83 (3H, d), 3.87 (3H, s), 5.26 (1H, q), 6.76 (1H, brs), 7.17 (1H, dd), 7.26–7.40 (6H, m), 7.70 (1H, dd), 7.98 (1H, s)

$^1$H-NMR data of compound No. 18 (CDCl₃); 1.55 (3H, d), 2.90 (3H, d), 3.90 (3H, s), 5.25 (1H, q), 6.77 (1H, br), 7.2–8.3 (9H, m)

$^1$H-NMR data of compound No. 20 (CDCl₃); 1.55 (3H, d), 2.88 (3H, d), 3.88 (3H, s), 5.22 (1H, q), 6.6 (1H, br), 7.16 (1H, m), 7.22 (2H, d), 7.38 (2H, m), 7.47 (2H, d), 7.68 (1H, m), 7.94 (1H, s)

$^1$H-NMR data of compound No. 21 (CDCl₃); 1.54 (3H, d), 2.89 (3H, d), 3.89 (3H, s), 5.20 (1H, q), 6.68 (1H, br), 7.18 (2H, m), 7.4 (4H, m), 7.68 (1H, m), 7.95 (1H, s)

$^1$H-NMR data of compound No. 23 (CDCl₃); 1.58 (3H, d), 2.88 (3H, d), 3.86 (3H, s), 5.30 (1H, q), 6.67 (1H, br), 7.15 (1H, dd), 7.35–7.55 (5H, m), 7.60 (1H, s), 7.68 (1H, dd), 7.96 (1H, s)

$^1$H-NMR data of compound No. 24 (CDCl₃); 1.57 (3H, d), 2.87 (3H, d), 3.86 (3H, s), 5.31 (1H, q), 6.63 (1H, br), 7.15 (1H, dd), 7.35–7.40 (2H, m), 7.46 (2H, d), 7.60 (2H, d), 7.67 (1H, dd), 7.97 (1H, s)

$^1$H-NMR data of compound No. 25 (CDCl₃); 1.56 (3H, d), 2.87 (3H, d), 3.88 (3H, s), 5.32 (1H, q), 6.82 (1H, br), 7.2–8.3 (9H, m), $^1$H-NMR data of compound No. 27 (CDCl$_3$); 1.59 (3H, d), 2.38 (3H, s), 2.85 (3H, d), 3.89 (3H, s), 5.26 (1H, q), 6.63 (1H, br), 7.08–7.30 (5H, m), 7.37 (1H, dd), 7.40 (1H, dd), 7.71 (1H, dd), 7.98 (1H, s)

$^1$H-NMR data of compound No. 28 (CDCl$_3$); 1.56 (3H, d), 2.34 (3H, s), 2.86 (3H, d), 3.88 (3H, s), 5.23 (1H, q), 6.58 (1H, br), 7.15 (1H, dd), 7.16 (2H, d), 7.24 (2H, d), 7.36 (1H, dd), 7.39 (1H, dd), 7.68 (1H, dd), 7.94 (1H, s)

$^1$H-NMR data of compound No. 29 (CDCl$_3$); 1.55 (3H, d), 2.30 (3H, s), 2.35 (3H, s), 2.86 (3H, d), 3.89 (3H, s), 5.47 (1H, q), 6.55 (1H, brs), 6.99 (1H, d), 7.02 (1H, d), 7.17 (1H, dd), 7.27 (1H, dd), 7.37 (2H, m), 7.70 (1H, dd), 7.94 (1H, s)

$^1$H-NMR data of compound No. 31 (CDCl$_3$); 1.56 (3H, d), 2.25 (3H, s), 2.27 (3H, s), 2.86 (3H, d), 3.88 (3H, s), 5.20 (1H, q), 6.60 (1H, brs), 7.1–7.2 (4H, m), 7.37 (2H, m), 7.70 (1H, dd), 7.94 (1H, s)

$^1$H-NMR data of compound No. 32 (CDCl$_3$); 1.24 (3H, t), 1.57 (3H, d), 2.64 (2H, q), 2.86 (3H, d), 3.87 (3H, s), 5.23 (1H, q), 6.56 (1H, br), 7.17 (1H, m), 7.18 (2H, d), 7.27 (2H, d), 7.37 (2H, m), 7.7 (1H, m), 7.95 (1H, s)

$^1$H-NMR data of compound No. 35 (CDCl$_3$); 1.28 (9H, s), 1.58 (3H, d), 2.86 (3H, d), 3.87 (3H, s), 5.27 (1H, q), 6.6 (1H, br), 7.16 (1H, m), 7.29 (2H, d), 7.38 (4H, m), 7.7 (1H, m), 7.95 (1H, s)

$^1$H-NMR data of compound No. 38 (CDCl$_3$); 1.57 (3H, d), 2.87 (3H, d), 3.81 (3H, s), 3.88 (3H, s), 5.22 (1H, q), 6.62 (1H, br), 6.90 (2H, d), 7.16 (1H, m), 7.30 (2H, d), 7.38 (2H, m), 7.69 (1H, m), 7.93 (1H, s)

$^1$H-NMR data of compound No. 39 (CDCl$_3$); 1.41 (3H, t), 1.56 (3H, d), 2.87 (3H, d), 3.89 (3H, s), 4.02 (2H, q), 6.6 (1H, br), 6.88 (2H, d), 7.16 (1H, m), 7.3 (2H, d), 7.38 (2H, m), 7.7 (1H, m), 7.93 (1H, s)

$^1$H-NMR data of compound No. 40 (CDCl$_3$); 1.03 (3H, t), 1.57 (3H, d), 1.8 (2H, q), 2.87 (3H, d), 3.89 (3H, s), 3.91 (2H, t), 5.21 (1H, q), 6.6 (1H, br), 6.9 (2H, d), 7.18 (1H, m), 7.3 (2H, d), 7.37 (2H, m), 7.7 (1H, m), 7.93 (1H, s)

$^1$H-NMR data of compound No. 42 (CDCl$_3$); 1.33 (6H, d), 1.56 (3H, d), 2.87 (3H, d), 3.89 (3H, d), 4.52 (1H, m), 5.21 (1H, q), 6.62 (1H, br), 6.85 (2H, d), 7.16 (1H, m), 7.27 (2H, d), 7.38 (2H, m), 7.70 (1H, m), 7.93 (1H, s)

$^1$H-NMR data of compound No. 44 (CDCl$_3$); 1.57 (3H, d), 2.50 (1H, t), 2.87 (3H, d), 3.88 (3H, s), 4.69 (2H, d), 5.21 (1H, q), 6.61 (1H, br), 6.97 (2H, d), 7.16 (1H, m), 7.30 (2H, d), 7.38 (2H, m), 7.70 (1H, m), 7.93 (1H, s)

$^1$H-NMR data of compound No. 49 (CDCl$_3$); 1.56 (3H, d), 2.88 (3H, d), 3.87 (3H, s), 5.57 (1H, d), 6.67 (1H, br), 7.13 (1H, d), 7.15 (1H, dd), 7.20 (1H, s), 7.28 (1H, d), 7.34–7.42 (3H, m), 7.68 (1H, dd), 7.96 (2H, s)

$^1$H-NMR data of compound No. 50 (CDCl$_3$); 1.57 (3H, d), 2.88 (3H, d), 3.87 (3H, s), 5.28 (1H, q), 6.64 (1H, br), 7.16 (2H, dd), 7.19 (2H, d), 7.38 (4H, m), 7.68 (1H, dd), 7.95 (1H, s)

$^1$H-NMR data of compound No. 54 (CDCl$_3$); 1.56 (3H, d), 2.88 (3H, d), 3.89 (3H, s), 4.35 (2H, q), 5.25 (1H, q), 6.64 (1H, br), 6.93 (2H, d), 7.17 (1H, dd), 7.32 (2H, d), 7.38 (2H, m), 7.70 (1H, dd), 7.93 (1H, s)

$^1$H-NMR data of compound No. 55 (CDCl$_3$); 1.57 (3H, d), 2.86 (3H, d), 3.89 (3H, s), 4.42 (2H, t), 5.23 (1H, q), 6.68 (1H, br), 6.93 (2H, d), 7.16 (1H, dd), 7.32 (2H, d), 7.38 (2H, m), 7.7 (1H, dd), 7.93 (1H, s)

$^1$H-NMR data of compound No. 56 (CDCl$_3$); 1.56 (3H, d), 2.86 (3H, d), 3.86 (3H, s), 5.29 (1H, q), 6.80 (1H, br), 7.14–7.21 (2H, m), 7.27 (1H, s), 7.33–7.45 (4H, m), 7.68 (1H, dd), 7.98 (1H, s)

$^1$H-NMR data of compound No. 58 (CDCl$_3$); 1.47 (3H, t), 1.56 (3H, d), 2.86 (3H, d), 3.24 (2H, q), 3.84 (3H, s), 5.27 (1H, q), 6.77 (1H, br), 7.14 (1H, dd), 7.18 (1H, d), 7.25 (1H, s), 7.29 (1H, d), 7.33–7.41 (3H, m), 7.66 (1H, dd), 7.96 (1H, s)

$^1$H-NMR data of compound No. 61 (CDCl$_3$); 1.56 (3H, d), 2.89 (3H, d), 3.89 (3H, s), 5.30 (1H, q), 6.66 (1H, br), 7.15 (1H, m), 7.38 (2H, m), 7.42 (2H, d), 7.64 (2H, d), 7.68 (1H, m), 7.96 (1H, m)

$^1$H-NMR data of compound No. 62 (CDCl$_3$); 1.54 (3H, d), 2.87 (3H, d), 3.87 (3H, s), 5.22 (1H, q), 6.64 (1H, br), 7.16 (1H, m), 7.22 (2H, d), 7.37 (2H, m), 7.47 (2H, d), 7.66 (1H, m), 7.94 (1H, s)

$^1$H-NMR data of compound No. 63 (CDCl$_3$); 1.62 (3H, d), 2.85 (3H, d), 3.87 (3H, s), 5.34 (1H, q), 6.60 (1H, br), 7.18 (1H, m), 7.3–7.7 (12H), 7.98 (1H, s) [Table 2]

$^1$H-NMR data of compound No. 76 (CDCl$_3$); 1.66 (3H, d), 2.78 (3H, d), 3.81 (3H, s), 5.42 (1H, q), 6.5 (1H, br), 7.15 (1H, m), 7.36 (2H, m), 7.5 (3H, m), 7.66 (1H, m), 7.8 (4H, m), 8.01 (1H, s)

$^1$H-NMR data of compound No. 78 (CDCl$_3$); 2.88 (3H, d), 3.88 (3H, s), 5.23 (2H, s), 6.82 (1H, br), 7.18 (1H, dd), 7.24 (1H, d), 7.33 (1H, d), 7.39 (1H, dd), 7.42 (1H, dd), 7.66 (1H, dd), 7.70 (1H, dd), 8.04 (1H, s)

$^1$H-NMR data of compound No. 80 (CDCl$_3$); 1.54 (3H, d), 2.89 (3H, d), 3.89 (3H, s), 5.18 (1H, q), 5.94 (2H, s), 6.65 (1H, br), 6.7–6.9 (3H, m), 7.16 (1H, m), 7.38 (2H, m), 7.69 (1H, m), 7.93 (1H, s)

$^1$H-NMR data of compound No. 81 (CDCl$_3$); 1.54 (3H, d), 2.89 (3H, d), 3.89 (3H, s), 4.25 (4H, s), 5.15 (1H, q), 6.66 (1H, br), 6.84 (2H, d), 6.88 (1H, d), 7.15 (1H, m), 7.38 (2H, m), 7.70 (1H, m), 7.92 (1H, s)

$^1$H-NMR data of compound No. 82 (CDCl$_3$); 1.64 (3H, d), 2.91 (3H, q), 3.92 (3H, s), 5.36 (1H, q), 6.75 (1H, br), 6.78 (2H, m), 7.19 (1H, m), 7.4 (2H, m), 7.75 (1H, m), 7.90 (1H, s) [Table 3]

$^1$H-NMR data of compound No. 86 (CDCl$_3$); 2.41 (3H, s), 2.46 (3H, s), 3.82 (3H, s), 4.03 (3H, s), 7.23–7.35 (3H, m), 7.48–7.54 (2H, m), 7.66 (1H, d), 7.73 (1H, s), 7.87 (1H, dd), 8.37 (1H, s)

$^1$H-NMR data of compound No. 87 (CDCl$_3$); 2.44 (3H, s), 3.81 (3H, s), 4.03 (3H, s), 7.26 (1H, dd), 7.31–7.43 (2H, m), 7.48–7.54 (2H, m), 7.76 (1H, d), 7.86 (1H, dd), 7.91 (1H, s), 8.37 (1H, s)

$^1$H-NMR data of compound No. 88 (CDCl$_3$); 2.49 (3H, s), 3.82 (3H, s), 4.03 (3H, s), 7.27 (1H, dd), 7.51 (2H, dd), 7.54 (1H, d), 7.67 (1H, d), 7.87 (1H, dd), 8.06 (1H, d), 8.19 (1H, s), 8.39 (1H, s)

$^1$H-NMR data of compound No. 91 (CDCl$_3$); 3.92 (3H, s), 4.06 (3H, s), 7.29 (1H, d), 7.49–7.62 (2H, m), 7.77 (2H, d), 8.10 (1H, d), 8.23 (2H, d), 8.38 (1H, s)

FORMULATION EXAMPLE 1

A wettable powder was obtained by uniformly pulverizing and mixing 20 parts of the compound No. 2 given in Table 1, 75 parts of diatomaceous earth and 5 parts of a surfactant comprising alkyl benzenesulfonate as a main component.

FORMULATION EXAMPLE 2

An emulsifiable concentrate was obtained by mixing and dissolving 30 parts of the compound No. 3 given in Table 1, 15 parts of "Sorpol®" 3005X (a nonionic surfactant/anionic surfactant mixture manufactured by Toho Chemical Industry Co., Ltd.) 25 parts of xylene and 30 parts of dimethylformamide.

To clarify the usefulness of the compounds of the present invention as an agricultural/horticultural fungicide, the following Test Examples will be given.

TEST EXAMPLE 1

Preventive activity on wheat powdery mildew

A wettable powder prepared in the same manner as described in Formulation Example 1 was diluted with water to a definite concentration and then applied by foliar application on what plants (var. Norin No. 61) at the 1 to 2 leaf stage grown in pots of 6 cm in diameter at a ratio of 10 ml/pot. After air-drying the chemical solution, a spore suspension of *Erysiphe graminis* (a pathogen of wheat powdary mildew) was inoculated to the plants by spraying. Then the plants were kept in a greenhouse for 7 to 10 days.

For evaluation, the diseased area ratio of each leaf was measured and the preventive value was calculated in accordance with the following formulae. The results are listed as "Preventive value 1" in Table 4.

$$\text{Preventive value (\%)} = \frac{(\text{average diseased area ratio in untreated plot}) - (\text{average diseased area ratio in treated plot})}{(\text{average diseased area ratio in untreated plot})} \times 100$$

The compound numbers correspond to the compound Nos. in Tables 1, 2 and 3.

TEST EXAMPLE 2

Preventive activity on what brown rust

A wettable powder prepared in the same manner as described in Test Example 1 was diluted with water to a definite concentration and then applied by foliar application on wheat plants (var. Norin No. 61) at the 1 to 2 leaf stage grown in pots of 6 cm in diameter at a ratio of 10 ml/pot. After air-drying the chemical solution, a spore suspension of *Puccinia recondita* (a pathogen of wheat brown rust) was inoculated into the plants by spraying. Then the plants were kept in a moist chamber at 22° C. for 15 hours and then allowed to stand in a greenhouse for 7 days.

For evaluation, the diseased area ratio of each leaf was measured and the preventive value was calculated in accordance with the following formula. The results are listed as "Preventive value 2" in Table 4.

$$\text{Preventive value (\%)} = \frac{(\text{average diseased area ratio in untreated plot}) - (\text{average diseased area ratio in treated plot})}{(\text{average diseased area ratio in untreated plot})} \times 100$$

The compound numbers correspond to the compound Nos. in Tables 1, 2 and 3.

TABLE 4

| Compound No. | Active ingredient (ppm) | Preventive value 1 (%) | Preventive value 2 (%) |
|---|---|---|---|
| 1 | 200 | 100 | 100 |
| 2 | 200 | 100 | 100 |
| 3 | 200 | 100 | 100 |
| 4 | 200 | 98 | 99 |
| 5 | 200 | 99 | 100 |
| 6 | 200 | 98 | 96 |
| 7 | 200 | 85 | 99 |
| 8 | 200 | 99 | 99 |
| 9 | 200 | 95 | 98 |
| 10 | 200 | 99 | 100 |
| 11 | 200 | 100 | 99 |
| 12 | 200 | 85 | 80 |
| 13 | 200 | 99 | 98 |
| 14 | 200 | 100 | 100 |
| 15 | 200 | 93 | 96 |
| 16 | 200 | 100 | 99 |
| 17 | 200 | 100 | 100 |
| 18 | 200 | 100 | 100 |
| 19 | 200 | 100 | 100 |
| 20 | 200 | 100 | 100 |
| 21 | 200 | 100 | 100 |
| 22 | 200 | 98 | 90 |
| 23 | 200 | 100 | 99 |
| 24 | 200 | 100 | 100 |
| 25 | 200 | 100 | 100 |
| 26 | 200 | 89 | 93 |
| 27 | 200 | 100 | 100 |
| 28 | 200 | 100 | 100 |
| 29 | 200 | 100 | 98 |
| 30 | 200 | 99 | 97 |
| 31 | 200 | 100 | 100 |
| 32 | 200 | 100 | 100 |
| 33 | 200 | 100 | 100 |
| 34 | 200 | 100 | 100 |
| 35 | 200 | 100 | 100 |
| 36 | 200 | 98 | 98 |
| 37 | 200 | 100 | 100 |
| 38 | 200 | 100 | 100 |
| 39 | 200 | 100 | 100 |
| 40 | 200 | 100 | 100 |
| 41 | 200 | 100 | 100 |
| 42 | 200 | 100 | 100 |
| 43 | 200 | 100 | 100 |
| 44 | 200 | 100 | 100 |
| 45 | 200 | 100 | 100 |
| 46 | 200 | 100 | 100 |
| 47 | 200 | 100 | 100 |
| 48 | 200 | 100 | 100 |
| 49 | 200 | 100 | 100 |
| 50 | 200 | 100 | 100 |
| 51 | 200 | 100 | 100 |
| 52 | 200 | 100 | 100 |
| 53 | 200 | 100 | 100 |
| 54 | 200 | 100 | 100 |
| 55 | 200 | 100 | 100 |
| 56 | 200 | 100 | 100 |
| 57 | 200 | 100 | 100 |
| 58 | 200 | 100 | 100 |
| 59 | 200 | 100 | 100 |
| 60 | 200 | 100 | 100 |
| 61 | 200 | 100 | 100 |
| 62 | 200 | 100 | 100 |
| 63 | 200 | 100 | 100 |
| 64 | 200 | 100 | 100 |
| 65 | 200 | 100 | 100 |
| 66 | 200 | 100 | 100 |
| 67 | 200 | 100 | 100 |
| 68 | 200 | 95 | 92 |
| 69 | 200 | 89 | 99 |
| 70 | 200 | 99 | 95 |
| 71 | 200 | 100 | 100 |
| 72 | 200 | 95 | 92 |
| 73 | 200 | 98 | 95 |
| 74 | 200 | 100 | 100 |
| 75 | 200 | 100 | 100 |
| 76 | 200 | 100 | 100 |
| 77 | 200 | 100 | 100 |
| 78 | 200 | 90 | 87 |
| 79 | 200 | 100 | 100 |
| 80 | 200 | 100 | 100 |
| 81 | 200 | 100 | 100 |
| 82 | 200 | 99 | 98 |
| 83 | 200 | 100 | 100 |
| 84 | 200 | 90 | 89 |
| 85 | 200 | 98 | 96 |

Residual activities were evaluated in cases simulating the practical uses as shown in following Test Examples.

The tests were performed on the compounds according to the present invention as well as ones described in the prior arts, in order to clarify the advancement of the present invention over prior arts.

TEST EXAMPLE 3

Residual activity on wheat powdery mildew

A wettable powder prepared in the same manner as described in Formulation Example 1 was diluted with water to a definite concentration and then applied by foliar application to wheat plants (var. Norin No. 61) at the 1 to 2 leaf stage grown in pots of 6 cm in diameter at a ratio of 10 ml/pot. After keeping outdoor for 14 days, the plants were inoculated with a spore suspension of *Erysiphe graminis* (a pathogen of wheat powdery mildew) by spraying. Then the plants were allowed to stand in a greenhouse at 20° to 22° C. for 7 to 10 days.

For evaluation, the diseased area ratio of each leaf was measured and the preventive value was calculated in accordance with the following formula. The results are listed as "Preventive value 3" in Table 5.

Preventive value (%) =

$$\frac{\text{(average diseased area ratio in untreated plot)} - \text{(average diseased area ratio in treated plot)}}{\text{(average diseased area ratio in untreated plot)}} \times 100$$

The compound numbers correspond to the compound Nos. in Tables 1, 2 and 3.

TEST EXAMPLE 4

Residual activity on wheat brown rust

A wettable powder prepared in the same manner as described in Test Example 1 was diluted with water to a definite concentration and then applied by foliar application to wheat plants (var. Norin No. 61) at the 1 to 2 leaf stage grown in pots of 6 cm in diameter at a ratio of 10 ml/pot. After keeping outdoor for 14 days, the plants were inoculated with a spore suspension of *Puccinia recondita* (a pathogen of wheat brown rust) by spraying. Then the plants were kept in a moist chamber at 22° C. for 24 hours and then allowed to stand in a greenhouse at 20° to 25° for 10 days.

For evaluation, the diseased area ratio of each leaf was measured and the preventive value was calculated in accordance with the following formula. The results are listed as "Preventive value 4" in Table 5.

Preventive value (%) =

$$\frac{\text{(average diseased area ratio in untreated plot)} - \text{(average diseased area ratio in treated plot)}}{\text{(average diseased area ratio in untreated plot)}} \times 100$$

The compound numbers correspond to the compound No. in Tables 1, 2 and 3.

TABLE 5

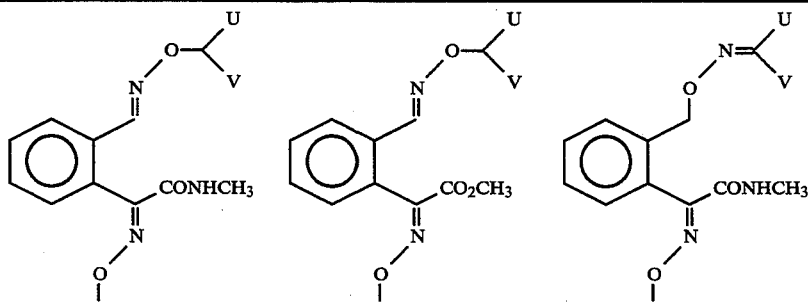

| U | V | | 250 | 50 (ppm) | 10 | 250 | 50 (ppm) | 10 | 250 | 50 (ppm) | 10 |
|---|---|---|---|---|---|---|---|---|---|---|---|
| H | 3-CF₃-Phenyl | Preventive value 3 | 100 | 62 | 12 | 86 | 0 | 0 | 70 | 0 | 0 |
| | | Preventive value 4 | 100 | 77 | 23 | 68 | 0 | 0 | 98 | 13 | 0 |
| | | referential patent No. | invention compound No. 1 | | | EP499823 | | | WO92/13830 | | |
| CH₃ | Phenyl | Preventive value 3 | 100 | 88 | 59 | 99 | 48 | 0 | 99 | 55 | 0 |
| | | Preventive value 4 | 100 | 85 | 11 | 99 | 36 | 0 | 98 | 38 | 0 |
| | | referential patent No. | invention compound No. 14 | | | EP499823 | | | EP463488 | | |
| CH₃ | 4-Cl-Phenyl | Preventive value 3 | 100 | 92 | 33 | 100 | 54 | 0 | 100 | 78 | 0 |
| | | Preventive value 4 | 100 | 97 | 27 | 95 | 31 | 0 | 100 | 83 | 0 |
| | | referential patent No. | invention compound No. 17 | | | EP499823 | | | EP463488 | | |
| CH₃ | 4-CH₃-Phenyl | Preventive value 3 | 100 | 82 | 23 | 88 | 0 | 0 | 99 | 50 | 0 |
| | | Preventive value 4 | 100 | 58 | 18 | 53 | 0 | 0 | 98 | 45 | 0 |
| | | referential patent No. | invention compound No. 28 | | | EP499823 | | | EP463488 | | |
| CH₃ | 4-CF₃-Phenyl | Preventive value 3 | 100 | 99 | 96 | 99 | 0 | 0 | 100 | 70 | 15 |
| | | Preventive value 4 | 100 | 96 | 91 | 99 | 24 | 0 | 99 | 77 | 28 |
| | | referential patent No. | invention compound No. 24 | | | EP499823 | | | EP463488 | | |
| CH₃ | 2-Naphthyl | Preventive value 3 | 100 | 99 | 95 | 85 | 20 | 0 | 92 | 77 | 0 |
| | | Preventive value 4 | 100 | 95 | 92 | 92 | 48 | 0 | 90 | 0 | 0 |
| | | referential patent No. | invention compound No. 76 | | | EP499823 | | | EP463488 | | |

TABLE 5-continued

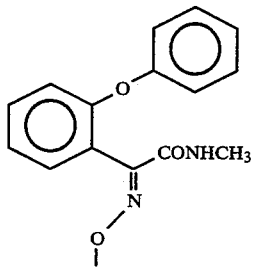

| | 250 | 50 (ppm) | 10 |
|---|---|---|---|
| Preventive value 3 | 52 | 8 | 0 |
| Preventive value 4 | 16 | 0 | 0 |
| referential patent No. | | EP398692 | |

Each of the compounds of the prevent invention is a novel one having an excellent fungicidal activity. It is particularly effective in controlling phytopathogenic fungi, which makes it highly useful as an agricultural/horticultural fungicide.

For example, these compounds exert high activity on rice blast (*Pyricularia oryzae*), rice sheath blight (*Rhizoctonia solani*) wheat powdery mildew (*Erysiphe graminis f. sp. tritici*) and barley powdery mildew (*E, graminis f. sp. hodei*), various leaf rusts of wheat and barley (e.g., *Puccinia recondita*), gray mold of vegetables and fruit trees (*Botrytis cinerea*) and late blight of various crops (*Phytophthora infestance*). Further, they have prolonged residual activity and excellent systemic action in plants, which makes them useful as an agricultural/horticultural fungicide.

While the invention has been described in detail and with reference to specific embodiments thereof, it will be apparent to one skilled in the art that various changes and modifications can be made therein without departing from the spirit and scope thereof.

What is claimed is:

1. A methoxyiminoacetic acid derivative represented by the following formula (I):

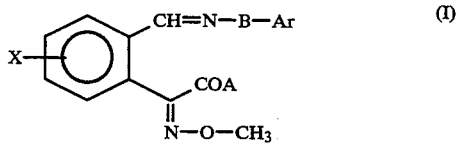

wherein X represents a hydrogen atom, a halogen atom, an alkyl group having 1 to 4 carbon atoms or an alkoxy group having 1 to 4 carbon atoms; A represents a methylamino group; B represents —O—$CR^1R^2$—, wherein $R^1$ and $R^2$ independently represent a hydrogen atom, an alkyl group having 1 to 4 carbon atoms, a cyano group or a trifluoromethyl group, and Ar represents an optionally substituted aryl group or an optionally substituted heteroaryl group.

2. The methoxyiminoacetic acid derivative as claimed in claim 1, wherein Ar represents an optionally substituted aryl group by 1 to 5 substituents which may be the same or different and, when the aryl group have 2 or more substituents, those adjacent to each other may be combined together to give a methylenedioxy or ethylenedioxy group and form a fused ring together with the aryl group, said substituents being selected from the group consisting of a cyano group; a halogen atom; an alkyl group having 1 to 6 carbon atoms; an alkenyl group having 2 to 4 carbon atoms optionally substituted by a halogen atom; a haloalkyl group having 1 to 4 carbon atoms; an alkoxy group having 1 to 6 carbon atoms optionally substituted by a halogen atom or a cycloalkyl group having 3 to 6 carbon atoms; an alkylcarbonyloxy group having 1 to 7 carbon atoms optionally substituted by a halogen atom; an acylamino group having 1 to 7 carbon atoms optionally substituted by a halogen atom; an alkylthio group having 1 to 6 carbon atoms optionally substituted by a halogen atom; an aryl group optionally substituted by an alkyl group having 1 to 4 carbon atoms or a halogen atom; an aryloxy group optionally substituted by an alkyl group having 1 to 4 carbon atoms or a halogen atom; an alkylsulfonyloxy group having 1 to 6 carbon atoms optionally substituted by a halogen atom; an alkenyloxy group having 2 to 6 carbon atoms optionally substituted by a halogen atom; and an alkynyloxy group having 2 to 6 carbon atoms; or an optionally substituted heteroaryl group by 1 to 2 substituents which may be the same or different, said substituents being selected from the group consisting of a cyano group; a halogen atom; an alkyl group having 1 to 6 carbon atoms; a haloalkyl group having 1 to 4 carbon atoms; and an alkoxy group having 1 to 6 carbon atoms optionally substituted by a halogen atom; or a cycloalkyl group having 3 to 6 carbon atoms.

3. An agricultural/horticultural fungicide containing a methoxyiminoacetic acid derivative as claimed in claim 2 as an active ingredient.

4. An agricultural/horticultural fungicide containing a methoxyiminoacetic acid derivative as claimed in claim 1 as an active ingredient.

5. A methoxyiminoacetic acid derivative represented by the following formula (II):

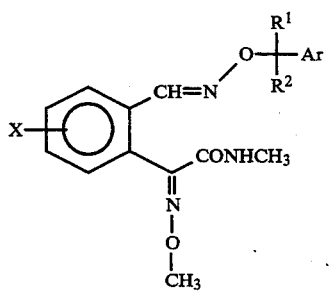

wherein X represents a hydrogen atom or a halogen atom; R¹ and R² independently represent a hydrogen atom, an alkyl group having 1 to 4 carbon atoms, a cyano group or a trifluoromethyl group; and Ar represents an optionally substituted aryl group or an optionally substituted heteroaryl group.

6. The methoxyiminoacetic acid derivative as claimed in claim 5, wherein X represents a hydrogen atom or a halogen atom; R¹ and R² independently represent a hydrogen atom, a cyano group or an alkyl group having 1 to 4 carbon atoms; and Ar represents an optionally substituted phenyl group or an optionally substituted naphthyl group, by one or more substituents being selected from the group consisting of a halogen atom; an alkyl group having 1 to 4 carbon atoms; an alkoxy group having 1 to 4 carbon atoms optionally substituted by a halogen atom; an acylamino group having 1 to 4 carbon atoms optionally substituted by a halogen atom; an alkylthio group having 1 to 3 carbon atoms; an alkylsulfonyloxy group having 1 to 3 carbon atoms optionally substituted by a halogen atom; or a trifluoromethyl group, or an optionally substituted thienyl group or an optionally substituted thiazolyl group, by one or more substituents selected from the group consisting of a halogen atom; an alkyl group having 1 to 4 carbon atoms; or a trifluoromethyl group.

7. An agricultural/horticultural fungicide containing a methoxyiminoacetic acid derivative as claimed in claim 6 as an active ingredient.

8. The methoxyiminoacetic acid derivative as claimed in claim 5, wherein X represents a hydrogen atom; R¹ represents a methyl group or a cyano group, and R² represents a hydrogen atom; and Ar represents a naphthyl group or an optionally substituted phenyl group by one or more substituents being selected from the group consisting of a halogen atom; an alkyl group having 1 to 4 carbon atoms; an alkoxy group having 1 to 4 carbon atoms optionally substituted by a halogen atom; an acylamino group having 1 to 4 carbon atoms optionally substituted by a halogen atom; an alkylsulfonyloxy group having 1 to 3 carbon atoms optionally substituted by a halogen atom; or a trifluoromethyl group.

9. The methoxyiminoacetic acid derivative as claimed in claim 8, wherein Ar represents an optionally substituted phenyl group by one ore more substituents being selected from the group consisting of a halogen atom; an alkyl group having 1 to 4 carbon atoms; an alkoxy group having 1 to 4 carbon atoms optionally substituted by a fluorine, an alkylsulfonyloxy group having 1 to 3 carbon atoms optionally substituted by a fluorine; or a trifluoromethyl group.

10. An agricultural/horticultural fungicide containing a methoxyiminoacetic acid derivative as claimed in claim 9 as an active ingredient.

11. An agricultural/horticultural fungicide containing a methoxyiminoacetic acid derivative as claimed in claim 5 as an active ingredient.

12. An agricultural/horticultural fungicide containing a methoxyiminoacetic acid derivative as claimed in claim 8 as an active ingredient.

13. The methoxyiminoacetic acid as claimed in claim 8, wherein R¹ represents a methyl group.

14. The methoxyiminoacetic acid as claimed in claim 13, wherein Ar represents a naphthyl group or a substituted phenyl group, the substituents being selected from the group consisting of one or two chlorines, trifluoromethyl, methyl and $C_1$–$C_2$ alkoxy optionally substituted by two or three fluorine atoms.

15. An agricultural or horticultural fungicide containing a methoxyiminoacetic acid derivative as claimed in claim 13 as an active ingredient.

16. An agricultural or horticultural fungicide containing a methoxyiminoacetic acid derivative as claimed in claim 14 as an active ingredient.

17. A method for controlling fungi, comprising the step of contacting the fungi or the materials, plants, seeds or soil threatened by fungal attack with a fungicidal amount of a compound as claimed in any one of claims 1–14.

* * * * *